(12) United States Patent
Loozen

(10) Patent No.: US 6,313,180 B1
(45) Date of Patent: *Nov. 6, 2001

(54) STEROID COMPOUNDS HAVING CONTRACEPTIVE AND ANTI-OSTEOPOROSIS ACTIVITY

(75) Inventor: Hubert Jan Jozef Loozen, Uden (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/538,783

(22) Filed: Mar. 30, 2000

Related U.S. Application Data

(63) Continuation of application No. 09/026,348, filed on Feb. 19, 1998, now Pat. No. 6,077,873.

(30) Foreign Application Priority Data

Feb. 21, 1997 (EP) .................................................. 97102884

(51) Int. Cl.⁷ .............................. A61K 31/56; C07J 53/00
(52) U.S. Cl. .................... 514/841; 514/169; 514/178; 514/179; 514/182; 552/514
(58) Field of Search .......................... 552/514; 514/169, 514/178, 179, 182

(56) References Cited

U.S. PATENT DOCUMENTS

| | | | |
|---|---|---|---|
| 5,162,312 | * 11/1992 | Kasch et al. | .......................... 514/179 |
| 5,407,928 | * 4/1995 | Kasch et al. | .......................... 514/179 |
| 6,077,873 | * 6/2000 | Loozen | .................................. 514/841 |

\* cited by examiner

*Primary Examiner*—Barbara P. Badio
(74) *Attorney, Agent, or Firm*—Michael G. Sullivan

(57) ABSTRACT

The invention relates to a steroid compound having the formula (I)

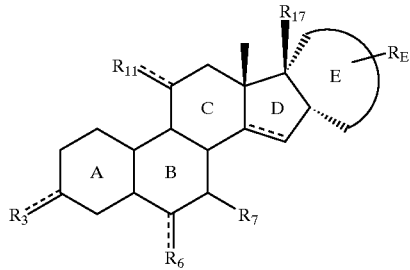

comprising a ring E, said ring sharing carbon atoms at position 16 and 17 with the five-membered ring D and being α with respect to said D-ring. In addition, the carbon atom at position 17 is substituted with an oxygen atom-comprising group through a CO bond. The invention also relates to a pharmaceutical composition comprising said steroid compound. The steroid compounds of the present invention are very suitable for use in the prevention or treatment of peri-menopausal or menopausal complaints, more preferably the prevention or treatment of osteoporosis. Furthermore, the steroid compounds of the present invention can be used for contraceptive purposes.

14 Claims, 6 Drawing Sheets

STEROID COMPOUNDS HAVING CONTRACEPTIVE AND ANTI-OSTEOPOROSIS ACTIVITY

This application is a continuation of U.S. Ser. No. 09/026,348, filed Feb. 19, 1998, now U.S. Pat. No. 6,077,873.

FIELD OF THE INVENTION

The present invention relates to a new class of steroid compounds, and in particular to a steroid compound having the formula (I)

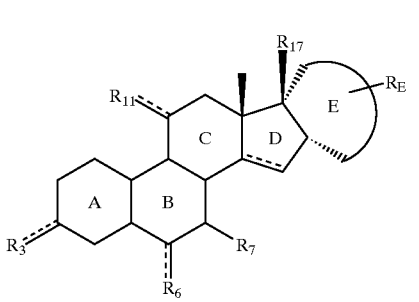

Formula (I)

wherein:

$R_3$ is =O; —OH; =NOR; —OR or —OOCR, in which R is an alkyl group having 1 to 6 carbon atoms;

$R_6$ is H; =$CH_2$ or —$(CH_2)_m$H with m is 1 or 2 wherein the steroid compound optionally may have one or more double bonds chosen from the group of $\Delta 9(10)$; $\Delta 5(10)$; $\Delta 4(5)$; $\Delta 11(12)$; $\Delta 14(15)$; or any of the rings A or B may be aromatic; The presence or absence of hydrogen atoms that have not been depicted, depends on whether a given ring is saturated, unsaturated, or aromatic, and is immediately evident to the normally skilled person.

$R_7$ is H; $C_{1-4}$-alkyl; $C_{2-5}$ alkenyl or $C_{2-5}$-alkynyl, wherein the alkyl, alkenyl or alkynyl group may be substituted with 1 to 3 halogen atoms independently selected from the group of fluorine and chlorine atoms;

$R_{11}$ is H; $C_{1-4}$-alkyl; $C_{2-4}$-alkenyl; $C_{2-4}$-alkynyl or $C_{1-4}$-alkylidene, wherein the alkyl, alkenyl; alkynyl or alkylidene group may be substituted with 1 to 3 halogen atoms independently selected from the group of fluorine and chlorine atoms;

E represents, including carbon atoms 16 and 17 of ring D, a four to seven-membered ring, said ring being a with respect to the D-ring, substituted with $R_E$ and optionally comprising one or two endocyclic double bonds; The α-position of ring E vis-à-vis ring D is essential, as the corresponding steroids having a ring E in the β-position do not possess the required biological activity. It should be noted that, for reasons of nomenclature, some compounds according to the invention have a name which includes a reference to 16β and/or 17β substituents. However, irrespective thereof, in all compounds of the invention, the E-ring as a whole is α.

$R_E$ is H; $C_{1-6}$-alkyl; $C_{2-6}$-alkenyl; $C_{2-6}$-alkynyl; $C_{1-6}$-alkylidene; $C_{2-6}$-spiro-annulated cycloalkyl; —OR; —SR; —OOCR; —NHR; —NRR; —NHCOR, wherein R (and in the case of $R_E$ being —NRR each R independently of the other) is an alkyl with 1 to 6 carbon atoms; —NCO; —$(CH_2)_n$—$N_3$ or —$(CH_2)_n$—CN, with n is 0 to 5, wherein the alkyl, alkenyl, alkynyl, alkylidene or cycloalkyl group may be substituted with 1 to 3 substituents independently selected from the group consisting of —OR; —SR; —OOCR; —NHR; —NRR; and —NHCOR, with R being defined as above, fluorine atoms and chlorine atoms;

$R_{17}$ is —OH; —$OCH_2OR$; —OR or —OOCR wherein R is an alkyl with 1 to 6 carbon atoms;

Any alkyl alkenyl, alkynyl and alkylidene groups in the steroid compound having the formula (I) may be branched or unbranched. If $R_3$, $R_6$ or $R_{11}$ is connected to the steroid skeleton through a single bond, the substituted carbon atom of the steroid skeleton either comprises a hydrogen atom or is involved in a double carbon-carbon bond. $R_E$ is connected to the E-ring through a single bond, the substituted carbon atom of the E-ring also comprises a hydrogen atom.

It was surprisingly found that the steroid compounds of the present invention have excellent and interesting estrogenic and/or progestagenic properties. Due to these specific characteristics, the steroid compounds of the present invention are very suitable for use in the prevention or treatment of peri-menopausal or post-menopausal complaints, including climacteric symptoms such as hot flushes and mood disturbances, urogenital complaints such as incontinence, skin (and vagina epithelium) atrophy, and other symptoms associated with estrogen-deficiency or estrogen withdrawal, such as osteoporosis, atherosclerosis, and Alzheimer's disease. The steroid compounds according to the invention are very suitable for the prevention or treatment of osteoporosis resulting from estrogen-deficiency.

Furthermore, the steroid compounds of the present invention can be used for contraceptive purposes.

BACKGROUND OF THE INVENTION

Steroid compounds having a 16, 17-ring substitution have been described. Chemical Abstracts 89: 215660p (Kamernitskii A V. et al.) describes a steroid compound comprising a 16,17 anellated 5- or 6-membered ring and an acetyl group at position 17. The compounds disclosed in this publication however differ from the steroid compounds according to the present invention in that the carbon atom at position 11 carries a hydrogen atom.

Chemical Abstracts 123: 285604t (Wang, J. et al.) discloses steroid compounds having a 10-membered E-ring with two triple bonds, a hydroxyl group at position 17, and a hydrogen atom at position 11.

EP 411.733 (Schering AG) discloses a steroid compound having a 6-membered E-ring, the carbon atom at position 17 being involved in a CO-bond. The compounds disclosed in EP 411733 however differ from the steroid compounds according to the present invention in that the carbon atom at position 11 carries a (substituted) aryl group. These compounds are disclosed to be competitive antagonists for progesterone.

SUMMARY OF THE INVENTION

Thus, none of this prior art references disclose the steroid compounds according to the present invention. The steroid compounds according to the present invention differ from those disclosed in the state of the art by the substitution at position 11, 16, and 17. More in particular, the steroid compounds according to the invention comprise a ring E, sharing carbon atoms at position 16 and 17 with the five-membered ring D and being α with respect to said D-ring. In addition, the carbon atom at position 17 is substituted with an oxygen atom-comprising group through a CO bond. The carbon atom at position 11 does not carry an aryl group.

Furthermore, none of the above publications suggests the interesting pharmaceutical properties of the steroid compound according to the present invention. Hence, the steroid compounds according to the present invention form a novel class of steroid compounds, as defined by their in vitro and in vivo activity.

Specifically for obtaining selective estrogen activities, in the steroid compounds according to the invention, the E-ring suitably is a five-membered ring. It is preferred that the E-ring is a six-membered ring, in view of the compounds' favourable estrogen/progestogen profiles, which include both potent, selective estrogens, and potent mixed estrogen/progestagen compounds. According to a preferred embodiment, the A-ring is aromatic and the remaining rings are saturated, wherein it is further preferred that $R_7$ is α-propyl. The most preferred compound, coded Org 38515, is further characterized in that $R_3$ and $R_{17}$ are OH, and $R_6$, $R_{11}$, and $R_E$ are H.

The present invention also relates to a pharmaceutical composition comprising the steroid compound according to the invention mixed with a pharmaceutically acceptable auxiliary, such as described in the standard reference, Gennaro et al., Remmington's Pharmaceutical Sciences, (18th ed., Mack publishing Company, 1990, see especially Part 8: Pharmaceutical Preparations and Their Manufacture.). The mixture of the steroid compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants. polymeric binders and the like is contemplated. In general any pharmaceutically acceptable additive which does not interfere with the function of the active compounds can be used. The steroid compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the steroid compound according to the invention for the manufacture of a medicament having a peri- and/or post-menopausal complaints relieving activity, in particular an anti-osteoporosis activity. Thus the invention also pertains to the medical indications of peri- and/or post-menopausal (climacteric) complaints and osteoporosis, i.e. a method of treatment in the field of HRT (hormone replacement therapy), comprising the administration to a patient, being a woman, of a compound as described hereinbefore (in a suitable pharmaceutical dosage form).

Further, the invention relates to the use of the steroid compound according to the invention for the manufacture of a medicament having contraceptive activity. Thus the invention also pertains to the medical indication of contraception, i.e. a method of contraception comprising the administration to a subject, being a woman or a female animal, of a compound as described hereinbefore (in a suitable pharmaceutical dosage form).

Finally the invention relates to the use of the steroid compound for the manufacture of a medicament having selective estrogenic activity, such a medicament being generally suitable in the area of HRT (hormone replacement therapy).

DETAILED DESCRIPTION OF THE INVENTION

The synthesis of the 16α,17α-anellated steroids is accomplished generally by first attaching a suitably functionalized C3 or C4 fragment to the $C_{16}$ α-position of the steroid (for formation of 5-membered or 6-membered rings respectively). To facilitate this process the 17-keto function is generally converted first into a dimethylhydrazone, which is cleaved off again after assembly of the required side chain functionality's. Ring closure can be brought about by organometallic techniques, such as the treatment of ω-iodoalkyl derivatives with transition metals like samarium (in the case of 5-membered rings, exemplified in example I), or by the formation of organolithium derivatives by use of reagents like t-butyllithium (exemplified for the formation of 6-membered rings in example II). Alternatively the formation of five membered rings can be brought about via generation of anions by fluoride assisted cleavage of silicon groups in ω-silyl side chains, as found in example III.

ω-Acetylenes can serve similarly well as substrates for ring closure reactions in radical anion mediated reactions, using elements like sodium or lithium as exemplified example IV.

An entirely different approach consists in formation of anellated rings by applying olefin metathesis techniques, using catalysts derived from transition metals like ruthenium, molybdenum or tungsten. To this end 16α, 17α dialkenylated steroids serve as substrates. They are easily available by alkylation of steroidal ketones at C-16, followed by introduction of an alkene fragment via organometallic anionic derivatives (lithiates etc.). As an example of such a reaction the formation of both 5- and 6-membered rings has been demonstrated in example V.

Thus, in addition to the above compounds of the invention and the various uses of these compounds, the invention also provides the above methods of making 16,17 anellated steroids by generating a ring added to a steroid skeleton, which ring includes carbon atoms 16 and 17 of said skeleton. These methods, which have not been applied in the art of steroid chemistry, allow making a broad range of 16,17 anellated steroids. E.g. in DE 19709870 (not pre-published) a method is described which has serious restrictions in respect of the specific compounds that can be synthesized. The method involves a [4+2] cycloaddition reaction of butadiene or dimethylbutadiene with a strongly activated double bond at $C_{16-17}$. This means that at $C_{17}$ always a strong electron-withdrawing substituent, such as —CN or -acyl, must be present, which seriously limits the number of options. Further, the method allows only 6-rings to be made, allows a limited number and variety of compounds, and requires a symmetric butadiene structure, as the methods lacks regioselectivity. The methods of the invention do not have these restrictions, and allow for the stereoselective and regioselective synthesis of a wide variety of 5- and 6-ring 16,17 anellated steroids as described hereinbefore. These methods thus make for an inventive contribution to the field of steroid chemistry.

The present invention will be illustrated by the following Figures and Examples without necessarily being restricted to the specific embodiments disclosed therein.

Figure 1:
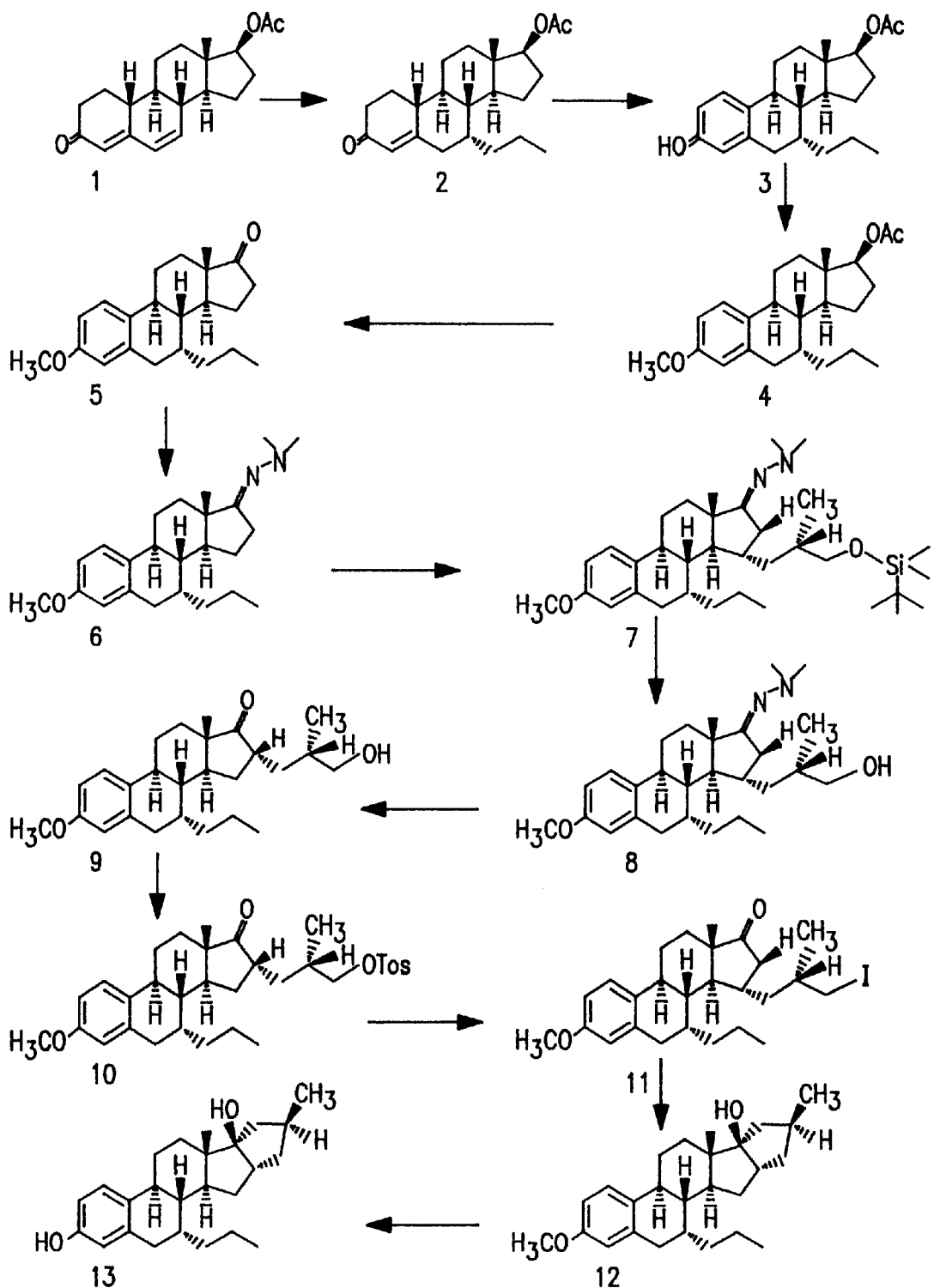
FIG. 1: schematic representation (2–13) of a process for the synthesis of two steroid compounds (12 and 13) according to the present invention as described in Example I.
Figure 2:
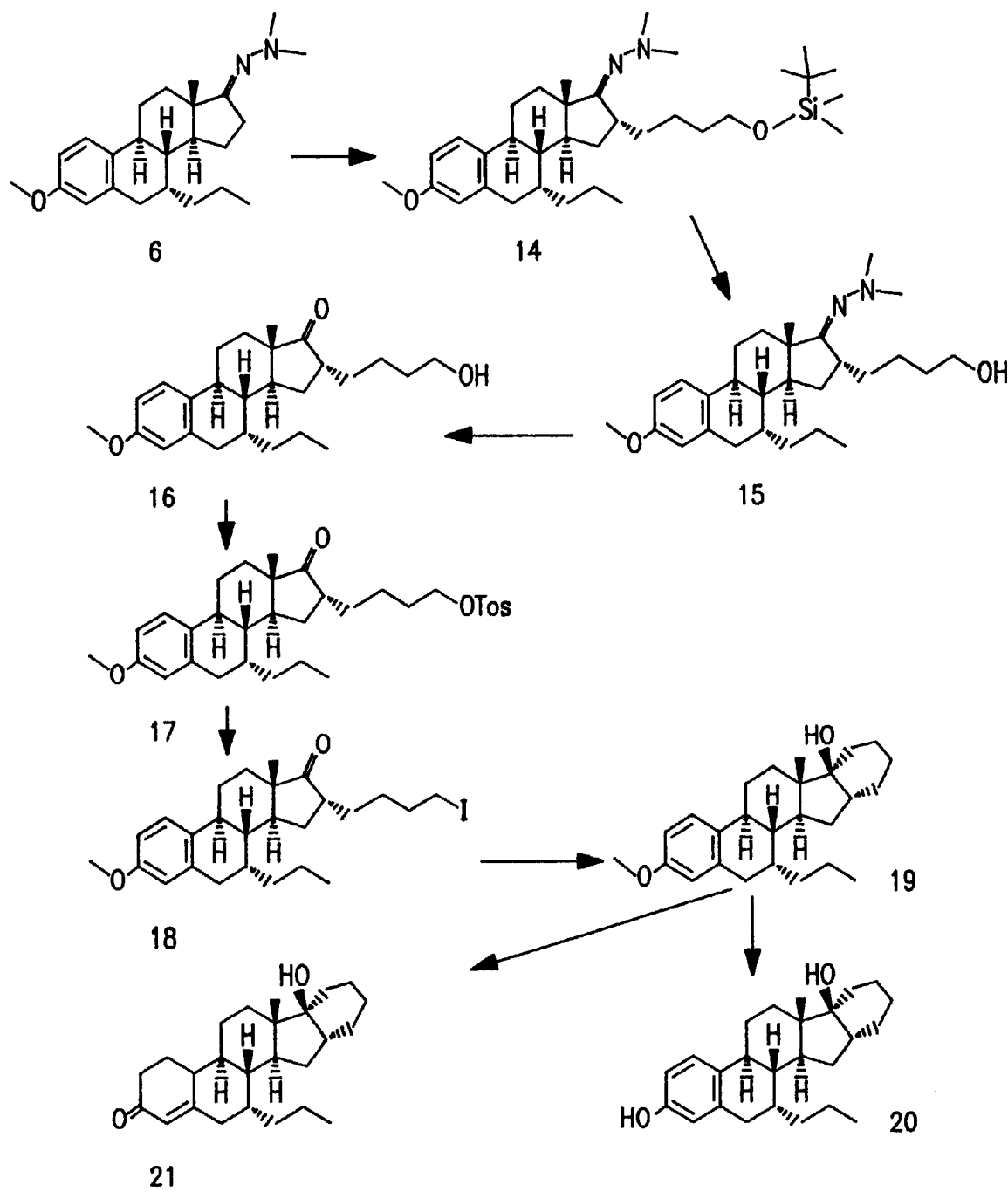
FIG. 2: schematic representation (14–21) of a process for the synthesis of three steroid compounds (19, 20, and 21) according to the present invention as described in Example II.
Figure 3:
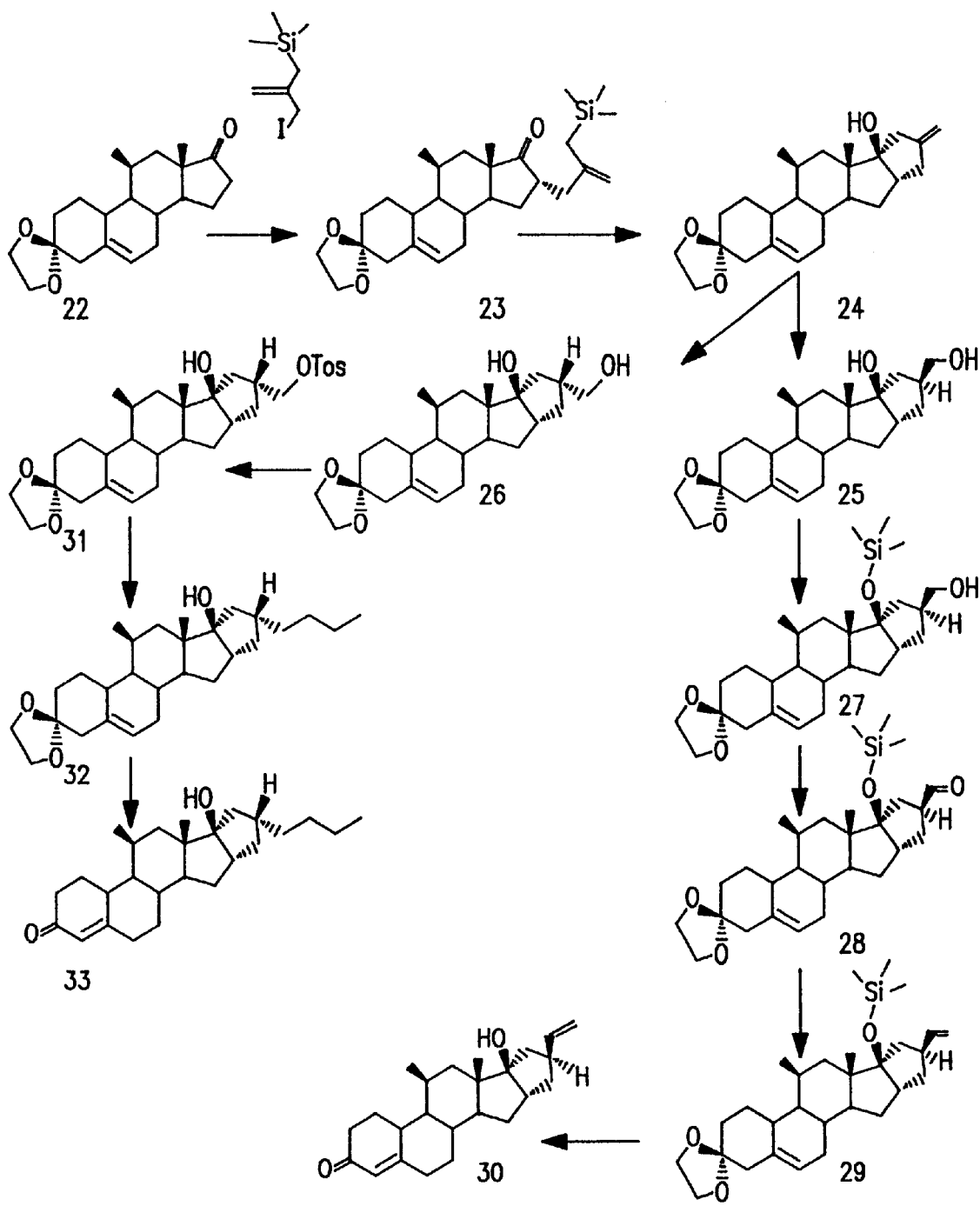
FIG. 3: schematic representation of a process (22–33) for the synthesis of two steroid compounds (30 and 33) according to the present invention as described in Example III.
Figure 4:
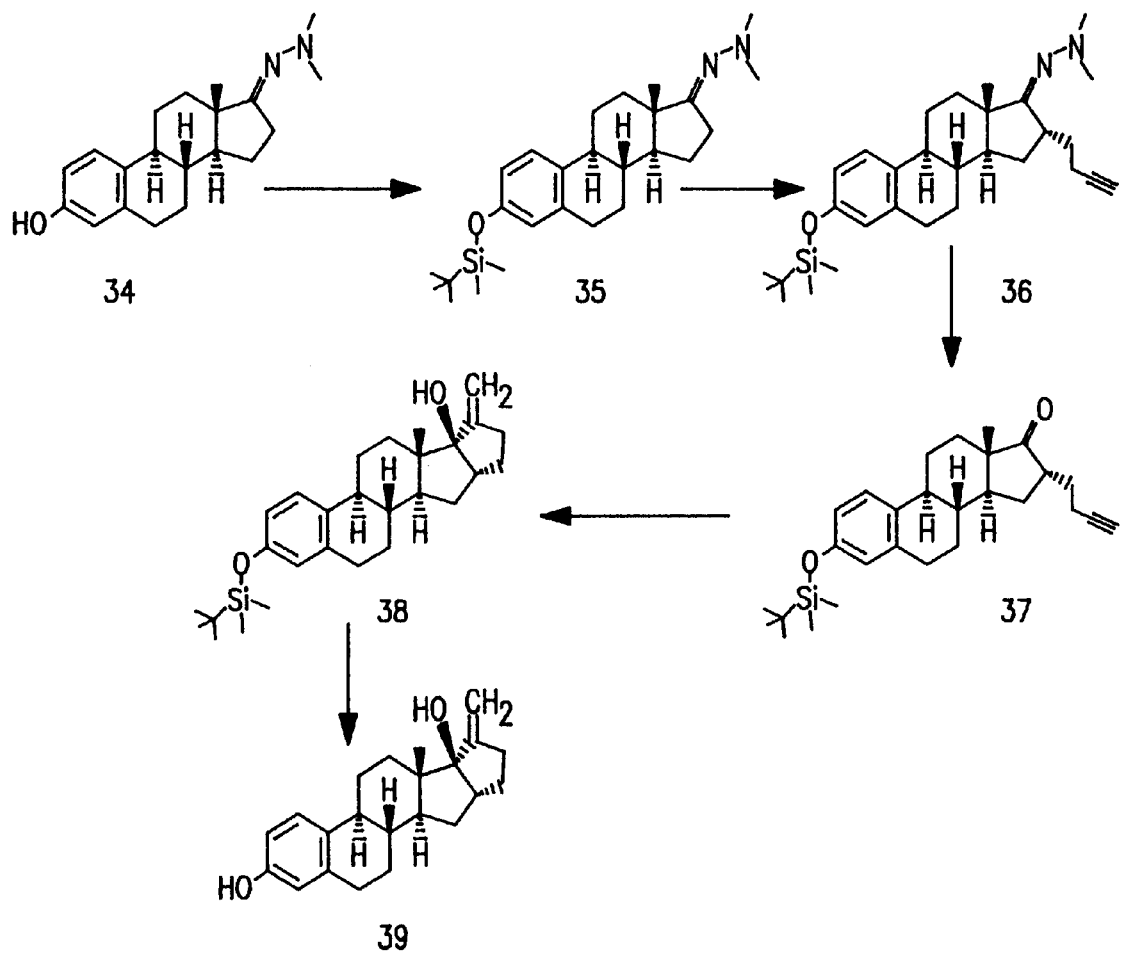
FIG. 4: schematic representation of a process (34–39) for the synthesis of a steroid compound (39) according to the present invention as described in Example IV.
Figure 5:
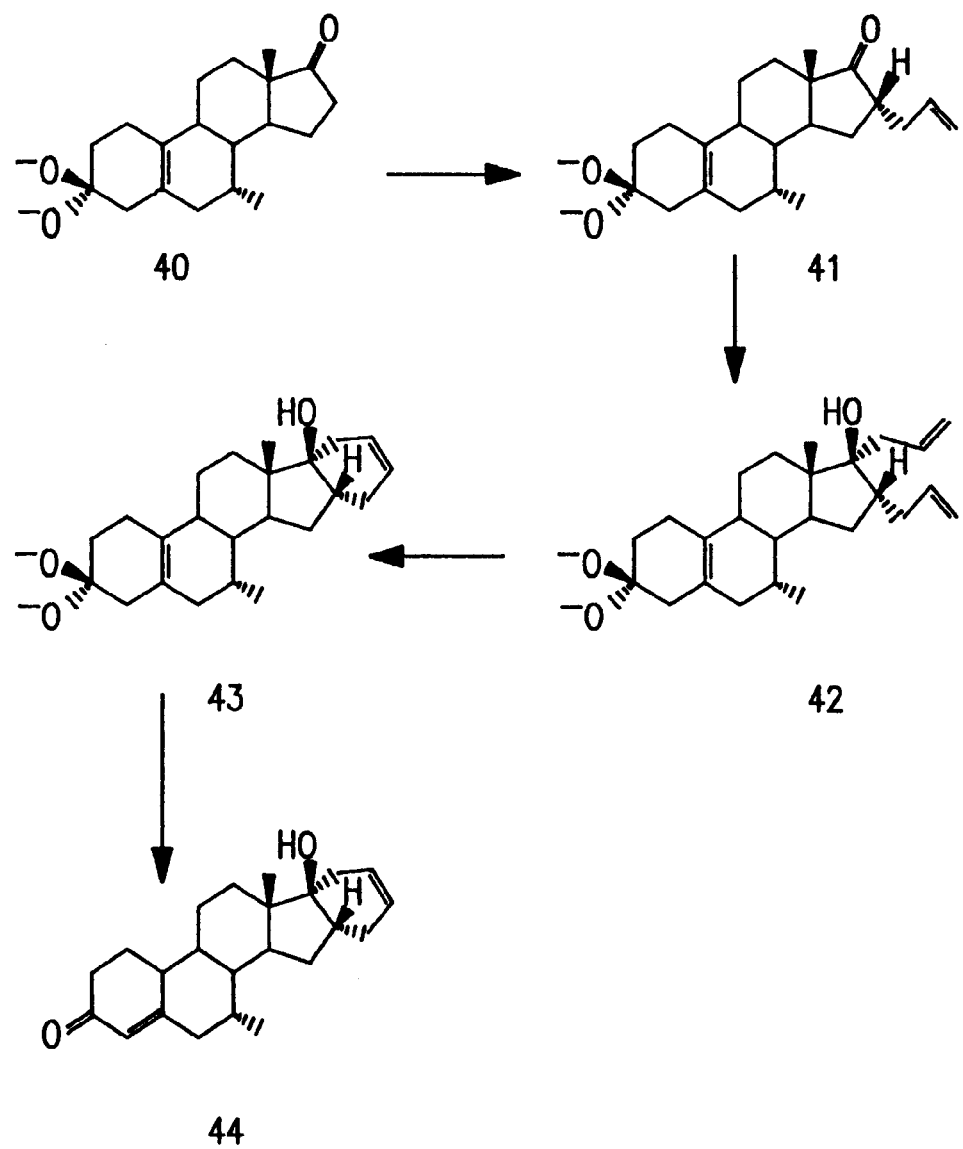
FIG. 5: schematic representation of a process (40–44) for the synthesis of a steroid compound (44) according to the present invention as described in Example V.
Figure 6:
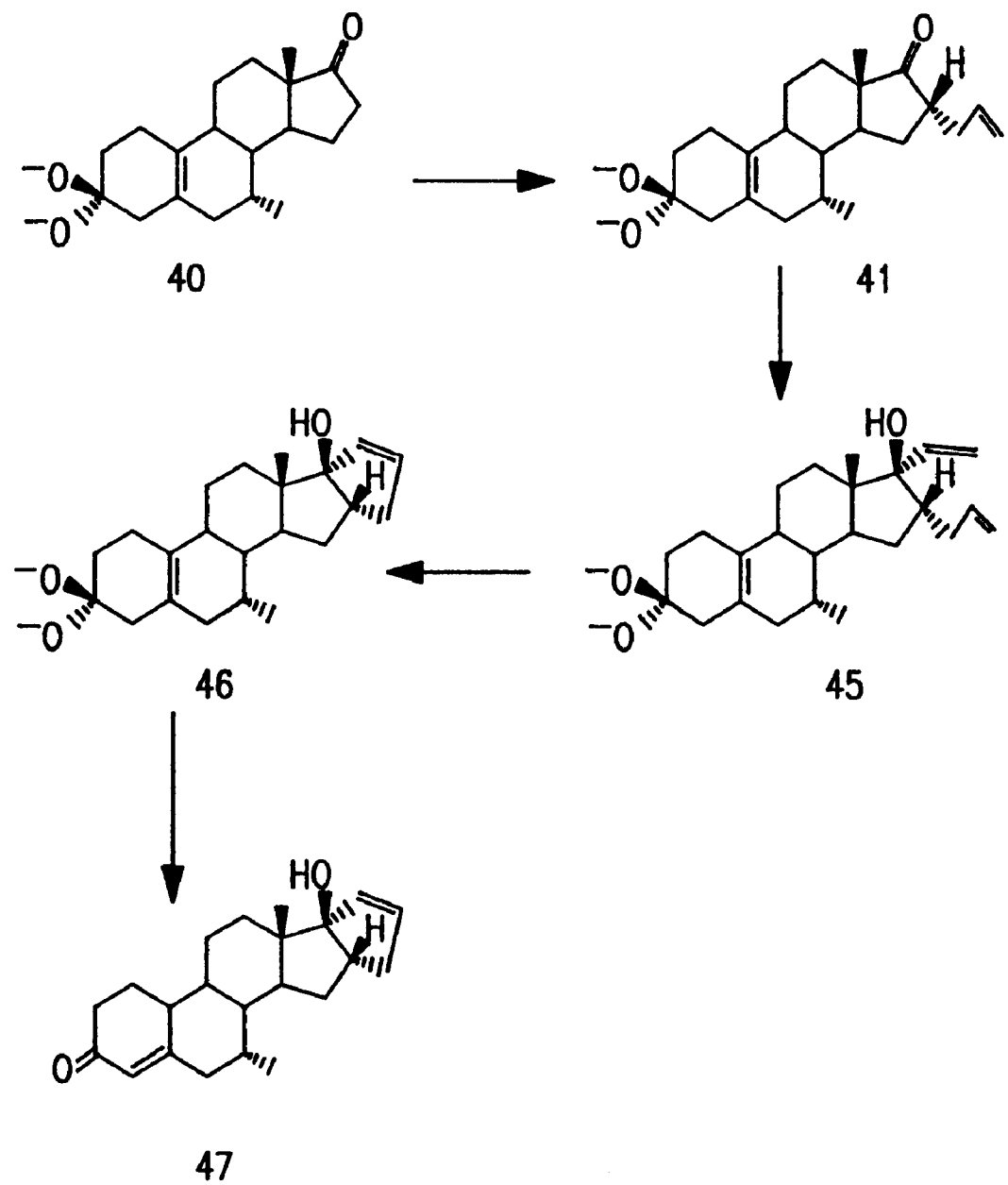
FIG. 6: schematic representation of a process (40–47) for the synthesis of a steroid compound (47) according to the present invention as described in Example VI.

The numbers between parentheses refer to the corresponding structural formula of compounds represented in the scheme.

EXAMPLE I

Although the required substrate 1 may be easily synthesized by dehydrogenation of steroids at C6C7 according to literature methods (e.g. by use of chloranil or DDQ) a new method was developed which allows a variety of 17-α-ethinyl, 17-β-hydroxy steroids to be used as well as substrates for gaining access to appropriate 17-keto steroids. They can be de-ethinylated by treatment with copper carbonate precipitated on Celite. Though a similar conversion has been described in literature using silver carbonate, the presently described method has the advantage of using a far more cheaper reagent. A batch of $CuCO_3$ on Celite was prepared as follows. A 100 gr of Celite was purified by stirring in a mixture of 500 ml of methanol and 100 ml of 6N HCl for 15 min. The mixture was filtered and washed several times with water until neutral. The material thus obtained was slurried into a solution of 60 g of $Cu(NO_3)_2.3H_2O$ in 400 ml of water. To this was then added dropwise with efficient stirring a solution of 30 g of $Na_2CO_3.H_2O$ in 200 ml of water. After stirring for an additional 15 min. the material was filtered and washed with water (In order to remove most of the water prior to drying, the material was slurried in acetone and filtered and subsequently washed with pentane) Drying was finally performed in vacuo at 80° overnight, to yield 160 g of reagent.

4 G of (17β)-17-hydroxypregna-4,6-dien-20-yn-3-one and 20 gr. of $CuCO_3$-Celite were suspended in 100 ml of toluene. The mixture was refluxed for about 6 hr with a Dean-Stark trap to remove some residual water. The progress of the reaction was monitored by tlc. After completion of the reaction the reaction mixture was filtered over Celite. The filtrate was concentrated and the residue treated with isopropylether-hexane to provide 2.4 g of pregna-4,6-dien-20-yn-3,17-dione, m.p. 182–184. Reduction of this with sodiumborohydride provided the required 17β alcohol, which upon acetylation with acetic anhydride provided the required substrate 1.

(7-alpha,17 beta)-17-(acetyloxy)-7-propylestr-4-en-3-one (2)

A solution of propyl lithium (prepared from 1.4 g of Li and 9 ml of propyl bromide in 60 ml of ether at −20 C) was added at −40 C to 7.6 g of CuI in 60 ml of dry THF.

After stirring for an additional 0.5 hr , a solution of 5.2 g of (17 beta)-17-(acetyloxy)estra-4,6-dien-3-one (1) in 20 ml of THF was added dropwise at −40 C. Upon stirring for an additional 15 minutes the reaction was complete, and the mixture was poured onto 300 ml of saturated $NH_4Cl$ solution, followed by extraction with ethyl acetate. The organic material, isolated after washing, drying and evaporation of the solvent, was taken up in 30 ml of THF and stirred in the presence of 3 ml of 6N $H_2SO_4$ to isomerize some Δ5,6 isomer to Δ4,5 isomer. After 1 hr the mixture was neutralized with saturated $NaHCO_3$ solution and extracted with ethyl acetate. Chromatography of the crude product over silica gel (heptane/ethyl acetate 8/2) provided 2.1 g of 2, m.p. 97–100° C.

(7-alpha,17-beta)-7-propylestra-1,3,5(10)-triene-3,17-diol 17-acetate (3)

To a solution of 15 g of 2 in 300 ml of acetoFitrile was added 12 g of $CuBr_2$. The mixture was stirred for 20 hr, while monitoring the reaction by TLC (tlc plates were purchased from Merck A.G., Germany). The reaction was then poured onto water and extracted with ethyl acetate. Chromatography of the crude product over a short silica gel column (heptaine/ethyl acetate 4/1 as eluent) provided 13.5 g of 3 as white amorphous material. $R_f$ 0.57 (hept/ethylac. 7/3).

(7-alpha, 17 beta)-3-methoxy-7-propylestra-1,3,5(10)-trien-17-ol acetate (4)

To a solution of 13.5 g of 3 in 60 ml of DMF was added 2.4 g of NaH (60% dispersion in mineral oil) in portions. After stirring for 1 hr hydrogen evolution had subsided. Then 3 ml of methyl iodide was added dropwise. After one hour stirring at ambient temperature, the reaction mixture was poured into 300 ml of water, and the product was extracted with ethyl acetate. The residue which remained after evaporation of the volatiles was taken up in 20 ml of THF and a solution of 4 g of NaOH in 80 ml of $CH_3OH$ was introduced. After stirring for 1 hr the saponification was complete. The reaction mixture was neutralized by addition of 1N $H_2SO_4$, and the product was extracted into ethyl acetate, to provide 11.5 g of 4, $R_f$ 0.34 (hept./ethylac. 7/3).

(7-alpha)-3-methoxy-7-propylestra-1,3,5(1)-trien-17-one (5)

To a solution of 10.4 g of 3-O-methyl, 7α-propylestradiol 4 in 50 ml of methylene chloride were subsequently added 15 g. of powdered sodium acetate, 30 g of silicagel and 32 g of pyridinium chlorochromate. After stirring for 1 hr the oxidation was complete. Excess reagent was destroyed by addition of 1 ml of isopropanol, followed by 150 ml of hexane 10 min. later. All the precipitates were filtered over Celite, and the filtrate was concentrated to dryness. This provided 9.6 g of essentially pure ketone 5; $R_f$ 0.54 (hept./ ethyl acetate 7/3).

(7-alpha)-3-methoxy-7-propylestra-1,3,5(10)-trien-17-one dimethylhydrazone (6)

To a solution of 11.2 g. of 7α-propyl-3-O-methylestrone 5 in 60 ml of toluene were added 6 ml of dimethylhydrazine and 0.5 ml. of trifluoroacetic acid.

The mixture was refluxed for 1.5 hr. After cooling to r.t. the reaction mixture was neutralized with 5% $NaHCO_3$ and the organic layer was washed several times with water and dried over sodium sulfate. After concentration and chromatography 11.4 g of the hydrazone 6 remained as an oil; $R_f$ 030 (hept/ethylac. 7/3).

[7-alpha,16-alpha (S)]-16-[3[[dimethyl(1,1-dimethylethyl) silyl]oxy]-2-methylpropyl]-3-methoxy-7-propylestr-1,3,5 (10)-trien-17-one dimethylhydrazone (7)

To a solution of 2.6 g of 6 in 30 ml of dry THF was added at −40° C. 5.6 ml of BuLi (1. 5 N solution in hexane). After stirring for 0.5 hr at this temperature 2.7 g of (2R)-2-methyl-3-iodopropanol-O-tert.butyldimethylsilyl (TBDMS) ether in 5 ml. of THF was introduced. After stirring for an additional hr at −20° C. the reaction mixture was poured into water and extracted. Subsequent chromatography provided 4.6 g of 7; $R_f$ 0.50 (hept./ethylac. 7/3 0.50).

[7-alpha,16alpha (S)]-16-(3-hydroxy-2-methylpropyl)-3-methoxy-7-propylestra-1,3,5(10)trien-17-one dimethylhydrazone (8)

A solution of 4.6 g of 7 in 5 ml of THF was treated with 15 ml of 1M TBAF in THF for 1 hr at 50° C. The mixture was diluted with 100 ml of water and extracted with ethyl acetate. After passing the product through a short silicagel column 3.1 g of 8 was obtained as an oil; $R_f$ 0.18 (hept./ethylac. 7/3).

[7-alpha,16-alpha(S)]-16-[2-methyl-3-[[(4-methylphenyl) sulfonyl]oxy]propyl]-7-propylestra-1,3,5(10)-trien-17-one (10)

A solution of 2.8 g of 9 in 7 ml of pyridine was treated at 0° C. with 2.6 g of tosyl chloride. After stirring for 2 hr. excess reagent was decomposed by stirring with ice for 0.5 hr. The product was extracted by ethylacetate and purified by chromatography, to provide 3.2 g of 10 as a colorless oil; $R_f$ 0.35 (hept./ethylac. 7/3).

[7-alpha,16-alpha(S)]-16-(3-hydroxy-2-methylpropyl)-3-methoxy-7-propylestra-1,3,5(10)trien-17-one (9)

A mixture of 3.1 g of 8 in 30 ml. of acetone and 3 ml of water was treated with 3 g of amberlyst-15 acidic resin (Fluka AG.) for 2 hr at 55° C. Thereafter the reaction mixture was filtered and concentrated, to provide 2.8 g of 9 as an oil; $R_f$ 0.75 (heptane/acetone 1/1).

[7-alpha-16-alpha,(S)]-16-(3-iodo-2-methylpropyl)-7-propylestra-1,3,5(10)-trien-17-one (11)

A mixture of 3.2 g of 10 and 10 g of sodium iodide in 30 ml of acetone was heated at 65° C. for 1 hr. After pouring the reaction into water and extraction with ethyl acetate 2.9 g of iodide 11 were obtained; $R_f$ 0.55 (hept./ethylac. 7/3).

(4'S,7-alpha,16beta,17-beta)-3,4',5',16-tetrahydro-3-methoxy-4'-methyl-7-propyl-17H-cyclopenta[16,17]estra-1,3,5(10)-trien-17-ol (12)

A solution of $SmI_2$ was prepared from 3 g of samarium metal and 4.7 g of 1,2-diiodoethane in 70 ml of dry THF. To this solution was added at 0° C. 20 mg of tris (dibenzoylmethanato)iron, followed by a solution of 2.8 g of 11 in 10 ml of THF. After stirring for an additional hr the mixture was poured onto water, acidified with $2N\ H_2SO_4$ and extracted with ether.

The crude product thus obtained was chromatographed to remove some 16,17-beta isomer, and provided 1.6 g of 12; $R_f$ 0.32 (hept/ethylac. 7/3).

The related beta isomer has a $R_f$ value of 0.37.

(4'S,7-alpha,16-beta, 17-beta)-3',4',5',16-tetrahydro-4'-methyl-7-propyl-17H-cyclopenta[16,17]estra-1,3,5(10)-trien-3,17-diol (13)

To a solution of 700 mg of 12 in 5 ml of toluene was added 15 ml of DIBAL (1M in toluene). The mixture was refluxed for 3 hr to effect ether cleavage. Excess reagent was destroyed by the addition of water, followed by further dilution with 40 ml of 2N HCl. The product was extracted with ethylacetate. After drying and concentration, the residue was triturated with diisopropyl ether, to provide 460 mg of crystalline 13; M.p. 166–168° C. $R_f$ 0.36 (hept./ethylac. 7/3).

EXAMPLE II (7-alpha,16-alpha)-16-[4-[[dimethyl(1,1-dimethylethyl) silyl]oxy]butyl]-3-methoxy-7-propylestra-1,3,5(10)-trien-17-one dimethylhydrazone (14)

To a solution of 3.9 g of the hydrazone 6 in 45 ml of dry THF was added at –60° C. 8.5 ml of 1.5N BuLi solution in hexane. After stirring for 0.5 hr a solution of 4.2 g of 4-iodobutanol-TBDMS ether in 5 ml of THF was added dropwise. The mixture was subsequently stirred at –20 for 1 hr and then poured into 200 ml of water and extracted with ethyl acetate.

Chromatographic purification over silica gel provided 6.2 g of 14 as an oil; $R_f$ 0.52 (hept./ethylac. 7/3).

(7-alpha,16-alpha)-16-(4-hydroxybutyl)-3-methoxy-7-propylestra-1,3,5(10)-trien-17-one dimethylhydrazone (15)

A solution of 6 g of 14 in 5 ml of THF was treated with 20 ml of 1M tetrabutylammonium fluoride in THF for 2 hr. The reaction was poured into water and extracted with ethyl acetate. After chromatography 4.1 g of 15 remained as an oil; $R_f$ 0.17 (hept./ethylace. 7/3).

(7-alpha,16-alpha)-16-(4-hydroxbutyl)-3-methoxy-7-propylestra-1,3,5(10)-trien-17-one (16)

A mixture consisting of 4 g of 15, 40 ml of acetone, 4 ml of water and 4 g of Amberlyst-15 acid resin was stirred for 2 hr at 50° C. The mixture was filtered, concentrated, taken up in 40 ml of toluene, dried and concentrated, to provide 3.7 g of essentially pure 16; $R_f$ 0.61 (hept/acetone 1/1); starting material $R_f$ 0.65.

(7-alpha,16-alpha-16-[4-[[(4-methylphenyl)sulfonyl]oxy] butyl]-7-propylestra-1,3,5(10)trien-17-one (17)

A mixture of 3.7 g of 16 and 3.2 g of tosylchloride in 10 ml of dry pyridine was stirred at 0–5° C. for 3 hr. After dilution with water the product was extracted with ethyl acetate. Chromatographic purification provided 4.6 g of tosylate 17; $R_f$ 0.45 (hept./ethylac. 7/3) 0.45.

(7-alpha,17-alpha)-16-(4-iodobutyl)-3-methoxn-7-propylestra-1,3,5(10)-trien-17-one (18)

A mixture of 4.6 g of 17 and 20 g of sodium iodide in 50 ml of acetone was heated at 60° for 1.5 hr. The reaction mixture was concentrated, diluted with water and extracted with toluene. After drying and concentration 4.4 g of iodide 18 remained as essentially pure material; $R_f$ 0.50 (hept./ethylac. 7/3).

(7-alpha. 16-alpha, 17-alpha)-3-methoxy-7-propyl-16,24-cyclo-19,21-dinorchola-1,3,5(10)trien-17-ol (19)

A solution of 3.8 g of the iodide 18 in 20ml of dry THF was treated at 3–60° C. with 9 ml of a 1.7M solution of tertbutyllithium in heptane. After stirring for an additional 15 min. at –60° C., the mixture was poured into water and extracted with ethyl acetate. The crude product obtained after removal of the volatiles was triturated with heptane, to provide 1.9 g of essentially pure 19; M.p. 161–162° C. $R_f$ 0.40 (hept./ethylac. 7/3).

(7-alpha,16-alpha,17-alpha)-17-hydroxy-7-propyl-16,24-cyclo-19,21-dinorchol-4-en-3-one (21)

To a solution of 1 g of lithium in 90 ml of liquid ammonia was added at –33° C. a solution of 1.3 g of 19 in 30 ml of dry THF. After stirring in refluxing ammonia for an additional 4 hr, the reaction was treated with 20 ml of ethanol followed by evaporation of the ammonia under a steady stream of nitrogen. The residue was diluted with 50 ml of water and extracted with ethylacetate. Concentration of the organic phase, followed by trituration of the residue with heptane, provided 1.1 g of pure dienolether intermediate; M.p. 190–192° C.

This material was dissolved in 25 ml of THF and treated with 5 ml of $6N\ H_2SO_4$. After stirring for 6 hr the mixture was neutralized with $Na_2CO_3$ and the product extracted with ethyl acetate. Chromatographic purification of the crude material thus obtained gave 610 mg of 21 as a white foam; $R_f$ 0.25 (hept/ethylac. 7/3).

(7-alpha,16-alpha,17-alpha)-7-propyl-16,24-cyclo-19,21-dinorchola-1,3,5(10)-trien-3,17-diol (20)

To a solution of 600 mg of 19 in 5 ml of dry toluene was added 12 ml of 1M DIBAH (diisobutylaluminum hydride) in toluene. After 2 hr of refluxing the demethylation was complete; excess reagent was destroyed by careful addition of water and subsequently the mixture was poured onto 50 ml of 4N hydrochloric acid, and the product extracted into ethyl acetate. The organic layer was dried, concentrated and the residue treated with diisopropylether, to provide 310 mg of 20; M.p. 240° C., $R_f$ 0.20 (hept./ethylac. 7/3)

EXAMPLE III (11-beta,16-alpha)-11-methyl-16-[2-[(trimethylsilylmethyl]
prop-2-enyl]estr-5-ene-3,17-dione 3-cyclic(1,2-ethanediyl)
acetal (23)

To a solution of 12.7 ml of hexamethyldisilazane in 50 ml of THF was added at −50° C. 40 ml of 1.5M BuLi in heptane solution. After stirring for 20 min. a solution of 16.5 g of 22 in 100 ml of THF was run in slowly at −50° C. After stirring for an additional 0.5 hr a solution of 25 g of 3-iodo-2-trimethylsilylmethylpropene in 25 ml of THF was introduced. The reaction mixture was stirred at −20° C. for an additional 3 hr, and then poured onto 400 ml of water. The product was extracted with ethyl acetate and chromatographed over silicagel. After trituration with heptane 12.5 g of product 23 was obtained; M.p. 184–185° C.; $R_f$ 0.55 (hept./ethylac. 7/3).

(11-beta,16-beta,17-beta)-4',5',16,17-tetrahydro-17-hydroxy-11-methyl-4'-methylene-3'H-cyclopenta[16,17]estra-5,16-dien-3-one 3-cyclic (1,2-ethanediyl acetal) (24)

A solution of 8.8 g of 23 in 200 ml of dry THF was treated with 4 ml of 1M tetrabutylammonium fluoride (TBAF) in THF. The mixture was refluxed for 15 min. to complete the ring closure reaction. An additional amount of 15 ml of 1M TBAF solution was then added and refluxing prolonged for 1 hr in order to cleave 17-O-silyl ether formed during the reaction. The mixture was subsequently concentrated to a small volume and diluted with water, followed by extraction with ethylacetate. Chromatographic purification provided 4.0 g of 24; M.p. 141–142° C., $R_f$ 0.28 (hept./ethylac. 7/3).

(4'S,11 -beta,16-beta,17-beta)-4',5',16,17-tetrahydro-17-hydroxy-4'-(hydroxymethyl)-11-methyl-3'H-cyclopenta[16,17]estra-5,16-dien-3-one 3-cyclic (1,2-ethanediyl acetal) (25), and its 4'R analog (26).

A solution of borabicyclononane (9-BBN) was prepared from 3 ml of 10M boranedimethylsulfide complex and 4 ml of 1,5-cyclooctadiene in 30 ml of dry THF. To this was added a solution of 3.8 g of 24 in 10 ml of THF.

The mixture was stirred for 2 hr and then excess reagent was destroyed by careful addition of 1 ml of ethanol, followed by 20 ml of 2N NaOH solution and 10 ml of 30%-$H_2O_2$. This mixture was stirred for another 3 hr and then further diluted with water and extracted with ethylacetate.

The crude product was chromatographed over silicagel (toluene/acetone as eluent) to provide 2.1 g of 25 (M.p. 178° C., $R_f$ 0.47 (tol./acet. 1/1)) and 1.2 g of 26 ($R_f$ 0.55 (tol./acet. 1/1)).

(4'R,11-beta,16-beta,17-beta)-4',5',16,17-tetrahydro-17-hydroxy-11-methyl-4-[[[(4-methylphenyly)sulphonyl]oxy]methyl]-3'H-cyclopenta[16,17]estra-5,16-dien-3-one-3-cyclic (1,2-ethandiyl acetal) (31)

A solution of 1.2 g of 26 and 0.8 g of to syl chloride in 5 ml of pyridine was stirred at 0–5° C. for 2 hr. Then the mixture was diluted with ice-water, stirred for 15 min. and extracted with ethyl acetate. Drying and concentration of the organic phase provided 1.6 g of essentially pure 31; $R_f$ 0.52 (tol./ethylac. 7/3).

(4'R,11-beta,16-beta,17-beta)-4'-butyl-4',5',16,17-tetrahydro-17-hydroxy-11-methyl-3'H-cyclopenta[16,17]estra-5,16-dien-3-one (32)

A cuprate reagent was prepared by adding 12 ml of a 2M propylmagnesiumbromide/ether solution to 2.3 g of CuI in 20 ml of THF at −20° C. After stirring for 15 min. a solution of 600 mg of 31 in 3 ml of THF was added. Stirring was continued for 2 hr more at −20° C. The reaction was worked up by addition of 60 ml of sat.$NH_4Cl$ and 10 ml of 10%-ammonia, followed by extraction with ethyl acetate.

The crude product was chromatographed, to provide 420 mg of 32; M.p. 97–98° C., $R_f$ 0.45 (hex./ethylacet. 7/3).

(4'R,11-beta,16-beta-17-beta)-4'-butyl-4',5',16,17-tetrahydro-17-hydroxy-11-methyl-3'H-cyclopenta[16,17]estra-4,16-dien-3-one (33)

A solution of 400 mg of 32 in 5 ml of acetone was treated with 2 ml of 4N $H_2SO_4$. After 2 hr at r.t. the mixture was diluted with water and extracted with ethyl acetate. Chromatographic purification afforded 360 mg of essentially pure 33 as an amorphous material; $R_f$ 0.27 (hept./ethylac. 7/3).

(4'S,11-beta,16-beta,17-beta)-4',5',16,17-tetrahydro-4'-(hydroxymethyl-11-methyl-17-[(trimethylsilyloxy]-3'H-cyclopenta[16,17]estra-5,16-dien-3-one 3-cyclic(1,2-ethanediyl acetal) (27)

The protection of the 17-OH function was performed in a multistep procedure. First the primary alcohol was acetylated. Thus, to a solution of 750 mg of 25 in 2 ml of pyridine was added 5 mg of 4-dimethylaminopyridine (DMAP), followed by 0.5 ml of acetic anhydride. After stirring for 1 hr. 10 g of ice-water was added, followed by extraction of the product with ethyl acetate. Concentration of the organic material, and treatment of the residue with heptane-diisopropylether provided 730 mg of monoacetate; M.p. 112° C. This material was dissolved in 3 ml of DMF containing 200 mg of irnidazole. Then 240 μl of TMS-chloride was added, and the mixture was stirred for 0.5 hr at room temperature. After addition of 15 ml of water, the product was extracted with ether. Upon drying and concentration 900 mg of essentially pure silylether derivative was obtained; $R_f$ 0.54 (hept./ethylac. 7/3).

This product was dissolved in 3 ml of dry THF and 70 mg of $LiAlH_4$ was added. After stirring for 10 min. the mixture was subsequently treated with 0.3 ml of water and 0.1 ml of 2N NaOH and 1 g of $NaSO_4$. Then it was filtered through Celite and concentrated to provide 700 mg of 27 as an amorphous material; $R_f$ 0.29 (hept./ethylac. 7/3).

(4'S, 11-beta, 16-beta,17-beta)-3,3-[1,2-ethanediylbis(oxy)]-4',5',16,17-tetrahydro-11-methyl-17-[(trimethylsilyl)oxy]-3'H-cyclopenta[16,17]estra-5,16-dien-4'-carboxaldehyde (28)

To a solution of 600 mg of 27 in 15 ml of methylene chloride was added 1.5 g of anhydrous sodium acetate, 2.5 g of silica gel followed by 2 g of pyridiniumchlorochromate. The mixture was stirred for 1 hr at room temperature. Then 50 ml of ether was added and after additional stirring for 15 min. the reaction was filtered through Celite, followed by evaporation of the volatiles, to provide 420 mg of essentially pure carboxaldehyde 28; a compound slowly solidifying on standing; $R_f$ 0.48 (hept./ethylac. 7/3).

(4'S,11-beta,16-beta,17-beta)-4'-ethenyl-4',5',16,17-tetrahydro-11-methyl-17-[(trimethylsilyl)oxy]3'H-cyclopenta[16,17]estra-5,16-dien-3-one 3-cyclic (1,2-ethanediyl acetal) (29)

To 1.3 g of methyltriphenylphosphonium chloride in 25 ml of TMF was added 1.7 ml of 1.5M BuLi in hexane solution at −40° C. After stirring for 30 min. 400 mg of 28 in 2 ml of THF was added. The mixture was allowed to warm to room temperature in about 0.5 hr and then quenched by pouring into 100 ml of water. The product was extracted with diethyl ether, and subsequently chromatographed to provide 280 mg of 29 as an oil; $R_f$ 0.53 (hept./ethylac. 7/3); starting material $R_f$ 0.23.

4'S,11-beta,16-beta,17-beta)-4'-ethenyl-4',5,'16,17-tetrahydro-11-methyl-17-hydroxy-3'H-cyclopenta[16,17]estra-4,16-dien-3-one (30)

A solution of 260 mg of 29 in a mixture of 3 ml of THF and 3 ml of 4N $H_2SO_4$ was stirred for 2 hr at 45° C. Then the reaction was neutralized with 5% NaHCO$_3$ solution and the product extracted into ethyl acetate.

Short path silica gel chromatography provided 150 mg of 30; R$_f$ 0.25 (hept./ethylac. 7/3).

EXAMPLE IV
3-[[(1,1-dimethylethyl)dimethylsilyl]oxy]estra-1,3,5(10)-trien-17-one dimethylhydrazone (35)

To a solution of 15.5 gr. of 3-hydroxyestra-1,3,5(10)-trien-17-one dimethylhydrazone (34) in 200 ml of DMF was added 13 gr. of imidazole, followed by dropwise addition of 15 gr. of TBDMSCl in 20 ml of ether. After stirring for an additional 16 hr the reaction mixture was poured onto 2 liters of water and the resulting mixture was stirred for an additional 10 minutes. The precipitate was filtered and dried in vacuo, to provide 20 g of 35, M.p. 100–103° C.

(16alpha)-3-[[(1,1-dimethylethyl)dimethylsilyl]oxy]-16-(4-butynyl)estra-1,3,5(10)-trien-17-one dimethylhydrazone (36)

The alkylation of the steroid was performed with the anion generated first of 4-bromo-1-butyne. The procedure was as follows. A solution of 11.9 gr. of 35 in 100 ml of THF was treated at –20° C. with 20 ml of a solution of 1.5M BuLi in hexane. After stirring for 1 hr at –20° C. the reaction mixture was cooled to –70° C. A cold solution of the anion of 4-bromo-1-butyne (prepared by addition of 36 ml of BuLi to 7.7 g of 4-bromo-1-butyne in 50 ml of THF at –78° C.) was added dropwise and the reaction mixture was allowed to warm up to room temperature. The mixture was then stirred for an additional 1 hr and then poured into 300 ml of 10% aq. NH$_4$Cl. The product was extracted with ethyl acetate. After chromatography 9.5 g of 36 was obtained as an oil. R$_f$ 0.85 (toluene/ethylacetate 6/4).

(16alpha)-3-[[(1,1-dimethylethyl)dimethylsilyl]oxy]-16-(4-butynyl)estra-1,3,5(10)-trien-17-one (37)

To a solution of 9 g of 36 in 100 ml of THF and 70 ml of 1M acetate buffer (pH 4,5) was added 15 g of periodic acid in 40 ml of ethanol. The mixture was stirred for 24 hr. Then 500 ml of water was added and the product was extracted with ethylacetate. Chromatography of the crude material thus obtained provided 4.2 g of 37.

(16alpha,17alpha)-3-[[(1,1-dimethylethyl)dimethylsilyl]oxy]-16,23-cyclo-19,24-dinorchola-1,3,5(10),20-tetraen-17-ol (38)

A solution of lithium naphtalenide was prepared from 3.4 g of naphtalene and 150 mg of lithium chips in 30 ml of dry THF. This solution was added dropwise to a solution of 560 mg of 37 in 5 ml of THF until a dark green color of the reaction mixture persisted. After stirring for an additional 10 minutes the reaction mixture was poured into 30 ml of NH4Cl and the product was extracted with ethyl acetate. Chromatographic purification provided 150 mg of crystalline 38.

(16alpha,17alpha)-16,23-cyclo-19,24-dinorchola-1,3,5(10),20-tetraene-3,17-diol (39)

A solution of 130 mg of 35 in 5 ml of 5% HCl in methanol was stirred for 2 hr at room temperature. The reaction mixture was then treated with 3 ml of pyridine and concentrated and diluted with 10 ml of water. The product was extracted in ethylacetate and finally purified by chromatography, to provide 65 mg of 39; M.p. 203–205° C.

EXAMPLE V
(7α,16α)-7-methyl-16-(prop-2-enyl)-estr-5(10)-ene-3,17-dione 3,3-dimethylacetal (41)

A solution of lithium diisopropylamide was prepared from 16.6 ml of 1.5M of butyllithium in hexane and 3.85 ml of diusopropylamine in 35 ml of THF at –20° C. After stirring for 20 min. a solution of 8.3 g of steroid 40 in 30 ml of THF was added and the mixture was stirred for 20 minutes at –20°. Then after cooling to –40°, 2.2 ml of allylbromide was added and then stirring was continued for an additional 4 hr at –20°, after which period tlc monitoring showed completion of the reaction. The mixture was quenched by addition of 200 ml of 5% NaHCO$_3$ solution, followed by extraction with ethylacetate. Chromatography over silicagel (hexane-5% ethylacetate as eluent) provided 7.2 g of 41 as a white solid; M.p. 85–86°.

(7α,16α,17β)-7-methyl-16,17-bis(prop-2-enyl)-17-hydroxy-estr-5(10)ene-3-one 3,3-dimethylacetal (42)

To a solution of 15 ml of 1 M allylmagnesium bromide in 30 ml of THF was added at –40° a solution of 4.5 g of 41 in 30 ml of THF. After stirring for 30 min. at this temperature, the mixture was poured onto 250 ml of 10% NH$_4$Cl solution and extracted with ethylacetate. The product thus obtained was chromatographed, to provide 3.2 g of the 16α,17α diallyl derivative 42 as white amorphous material.

(7α,16α,17α)-7-methl-17-hydroxy-16,24-cyclo-19,21-dinorchola-5(10),22-dien-3-one 3,3-dimethylacetal (43)

To a solution of 1.3 g of 42 in 30 ml of methylenedichloride was added 200 mg of bis(tricyclohexylphosphine) benzylideneruthenium dichloride. The reaction was stirred until completion. The solvent was removed partially by concentration and the residual material chromatographed on a silicagel column to provide 1.1 g of 43 as an amorphous white material. R$_f$=0.38 (heptane/ethyl acetate 7/3 v/v).

(7α,16α,17α)-7-methyl-17-hydroxy-16,24-cyclo-19,21-dinorchola-4,22-dien-3-one (44)

A solution of 1 g of 43 in 30 ml of acetone was treated with 5 ml of 2N HCl. After stirring for 2 hr at room temperature the reaction was complete. After neutralization with 5% NaHCO$_3$ solution the mixture was extracted with ethyl acetate and the product passed through a short silicagel column. The product thus obtained was treated with diisopropylether, to provide 0.65 g of 44; M.p. 130–131; R$_f$ (heptane/ethylacetate 7/3) 0.14.

EXAMPLE VI
(7α,16α,17α)-7-methyl-16-(prop-2-enyl)-17-hydroxypregna-5(10),20-dien-3-one 3,3-dimethylacetal (45)

A solution of vinyllithium was prepared by addition of 0.8 ml of a 1.6M solution of butyllithium in hexane to 0.32 ml of vinyltributyltin in 3 ml of THF at –50° C. After stirring for 20 min. a solution of 300 mg of 41 in 2 ml of THF was added dropwise. Upon stirring for an additional 15 min. the mixture was quenched by addition of 20 ml of 10% NH$_4$Cl solution, followed by extraction of the product into ethylacetate. Subsequent chromatographic purification provided 120 mg of 45 as an amorphous material; R$_f$ 0.56 (heptane/ethylacetate 7/3 v/v).

(7α,16β,17β)-16,17-dihydro-17-hydroxy-5'H-cyclopenta[16,17]estra-5(10),16-dien-3-one 3,3-dimethylacetal (46)

To a solution of 120 mg of 45 in 4 ml of methylene dichloride was added 30 mg of bis(tricyclohexylphosphine) benzylideneruthenium dichloride. After stirring for 2 hr the mixture was concentrated and filtered through a silica gel column, to provide 80 mg of 4.6 R$_f$ 0.40 (heptane/ethyl acetate 7/3 v/v).

(7α,16β,17β)-7-methyl-16,17-dihydro-17-hydroxy-5'H-cyclopenta[16,17]estra-4,16-dien-3-one (47)

A solution of 80 mg of 46 in 2 ml of acetone was treated with 0.2 ml of 2N HCl. After stirring for 2 hr at room temperature the reaction mixture was neutralized by addition of $NaHCO_3$, and diluted with water. The product was extracted with ethylacetate and passed through a short silica column, to provide 45 mg of 47. Mp 175–176° C., $R_f$ 0.49 (heptane/ethylacetate 1/1 v/v).

EXAMPLE VII

Test for Prevention of Ovariectomy-induced Bone Loss in Rats (anti-osteoporosis test)

Introduction

Ovariectomy induces in rats bone loss, which is due to oestrogen deficiency. Administration of oestrogenic compounds prevents this effect. The test is used to evaluate a compound for anti-osteoporotic activity in ovariectomised rats. The effect on bone mass can be evaluated by peripheral Quantitave Computed Tomography (pQCT) measurement of trabecular bone mineral density.

Test Animal

Mature virgin female Wistar rats preferentially, 225–250 g. Strain: Hsd/Cpd:Wu, SPF-bred by Harlan, CPB, Zeist, The Netherlands.

Experiment

On day 1 of the experiment the rats are weighed and distributed over the cages in order of body weight. The rat with the lowest body weight in the first cage and the heaviest rat in the last cage. Treatments are randomized over the rats per block. A block (group of 3+n treatments) consists of 1 Intact placebo rat, 1 OVX placebo rat, 1 OVX reference rat and 1 rat of each n treatments.

Sham-operation and ovariectomy are performed under ether anaesthesia. After recovery from the anaesthesia, within 24 h, vehicle, reference compound or test compound is administered once or twice daily for 4 weeks.

Bone mineral density measurement by pQCT

Trabecular bone mineral density ($mg/cm^3$) of the metaphyseal part of the femur was measured with a pQCT (peripheral Quantitative Computed Tomography machine; XCT 960A, Stratec, Birkenfeld, Germany) directly after autopsy on fresh tissue. Two 360° scans, which have, due to the X-ray beam, a standard thickness of 1 mm were taken. The scans have a resolution of 0.148×0.148 mm. One scan was taken at 5.5 mm from the distal end of the femur, where trabecular bone mineral density of the metaphyseal part was measured. The other scan was taken in the diaphysis at 13.5 mm from the distal end, which contains no trabecular bone. In the latter scan cortical bone mineral density and the geometrical parameters, such as cortical thickness, total bone area, outer and inner diameter, were determined. Intra- and inter-assay variation for the measurement of trabecular bone mineral density in the distal femur were about 2–3%. The XCT-960A was calibrated with a standard of hydroxyapatite embedded in acrylic plastic.

Interpretation of Results

Ovariectomy causes a statistically significant decrease in trabecular bone mineral density ($P \leq 0.05$, 2 way ANOVA). Test compounds are considered to be active when mean bone mineral density values of the distal femur are significantly increased as compared to the ovariectomised control group.

The active dose ($ED_{50}$) is the dose where a mean proportional difference in trabecular bone mineral density between 40 and 60% is reached as compared to the sham and ovariectomised group.

References

Wronski T. J. and Yen C. F.: The ovariectomised rat as an animal model for postmenopausal bone loss. Cells and Materials, Supp. 1 (1991): 69–76.

Yamazaki I. and Yamaguchi H.: Characteristics of an ovariectomised osteopenic rat model. J. Bone Min. Res. 4 (1989): 12–22.

Ederveen A. G. H., Spanjers C. P. M., Quaijtaal J. H. M. and Kloosterboer H. J.: Effect of treatment with tibolone (Org OD 14) or 17α-ethinyl estradiol on bone mass, bone turnover and biomechanical quality of cortical and trabecular bone in mature ovariectomised rats. Osteoporosis Int. in press, 1998.

EXAMPLE VIII

Test for Receptor-binding In vitro

The relative progesterone receptor binding affinity of the compounds of the invention was measured for cytoplasmic progesterone receptors present in human breast tumor cells (MCF-7 cells, incubation time 16 h., temperature 4° C.) and compared with the affinity of (16α)-16-ethyl-21-hydroxy-19-norpregn-4-ene-3,20-dione (according to the procedure described by E. W. BerGink et al., J. Steroid Biochem., Vol. 19, 1563–1570 (1983)). The relative estradiol receptor binding affinity was measured in the same manner as described above but using 17βestradiol as a reference.

Test for Estrogenic Activity In vivo

The in vivo estrogenic activity was determined by means of the well known Allen Doisy test, described in F. Allen, L. A. Doisy, J. Amer. Med. Assoc., 81,819–821 (1923).

Test for Proyestaienic Activity In vivo

The in vivo progestagenic activity was determined by means of the well known McPhail test, described in McPhail, M. K.: The assay of progestin, Journal of Physiology, 1934, 83:145–156.

Several of the compounds according to the Examples I–VI, as well as other compounds according to the invention synthesized in analogous manner, were subjected to the tests described in the Examples VII and VIII. The results are described in the Table, in which the type of A-ring and the substitution at carbon atoms nos. 7, 11, and 17 is indicated. In the columns captioned E and P, the relative binding affinities for the estrogen and progesterone receptors are given; the $ED_{50}$ results of the AllenDoisy and the McPhail tests have been indicated in μg/kg. In the column captioned "Osteoporosis", the $ED_{50}$ results of the anti-osteoporosis test are given (dose in μg/kg, day, as described above).

Table Representing The Relative Binding Affinities To The Human Estradiol (E)
Or Progesterone (P) Receptor And
The In Vivo Hormonal Activities (ED$_{50}$) Upon Oral Administration

| A-ring | 7α | 11β | 16α,17α | Code | E (%) | P (%) | AllenDoisy (μg/kg) | McPhail (μg/kg) | Osteoporosis (μg/kg, day) |
|---|---|---|---|---|---|---|---|---|---|
| Δ4 = 5 | H | H | 5-ring + 4'S-methyl | 38541 | | 58 | >500 | 125 | >1000 |
| Δ4 = 5 | H | H | 5-ring + 4'S propyl | 37977 | | 151 | >4000 | 500 | >1000 |
| Δ4 = 5 | H | H | 6-ring | 37518 | | 115 | >4000 | 125 | >2000 |
| Δ4 = 5 | H | methyl | 5-ring + 4'R-butyl | 38276 | | 115 | >500 | 125 | >1000 |
| Δ4 = 5 | H | methyl | 5 ring + 4'S azidomethyl | 38322 | | 44 | >500 | 63 | >1000 |
| Δ4 = 5 | H | ethyl | 6-ring | 37943 | | 96 | 192 | 1000 | 400 |
| Δ4 = 5 | H | ethyl | 5 ring + 4'S-ethyl | 38610 | | 0.3 | 32 | >125 | 125 |
| Δ4 = 5 | H | ethyl | 5-ring + 4'S-propyl | 38577 | | 139 | 192 | >500 | 250 |
| Δ4 = 5 | methyl | H | 5-ring | 37352 | | 36 | 1000 | 250 | 500 |
| Δ4 = 5 | propyl | H | 5-ring + 4'R methyl | 38550 | | 36 | 125 | >125 | 125 |
| Δ4 = 5 | methyl | H | 5-ring + 4"S methyl | 38049 | | 250 | >2000 | 1000 | >1000 |
| Δ5 = 10 | methyl | H | 5-ring | 37351 | | 4 | 4000 | 2000 | 1000 |
| Δ5 = 10 | H | ethyl | 5-ring + 4'R propyl | 38151 | | 8 | 125 | >1000 | ND |
| Δ5 = 10 | H | H | 6-ring | 37516 | | 13 | >4000 | 1000 | >2000 |
| aromatic | H | H | 6-ring | 37469 | 1 | 23 | >4000 | >2000 | >4000 |
| aromatic | H | H | 5-ring + 4'R-propyl | 37968 | 1 | 6 | >1000 | >4000 | ND |
| aromatic | H | H | 5-ring + 4'S-propyl | 37969 | 3 | 25 | >1000 | 4000 | >1000 |
| aromatic | H | ethyl | 6-ring | 37862 | 96 | 2 | 32 | ND | <16 |
| aromatic | methyl | H | 5-ring + 4'S-methyl | 37893 | 38 | 11 | 500 | >4000 | 500 |
| aromatic | methyl | H | β 5-ring + 4'S-propyl | 38079 | <1 | 1 | >4000 | ND | ND |
| aromatic | methyl | H | 6-ring | 37828 | 11 | 10 | 192 | — | 500 |
| aromatic | propyl | H | 5-ring + 4'R-methyl | 38514 | 11 | 4 | 24 | >2000 | <32 |
| aromatic | propyl | H | 5-ring + 4'S-methyl | 38481 | 23 | 6 | 64 | >4000 | 125 |
| aromatic | propyl | H | 6-ring | 38515 | 16 | 10 | 96 | 4000 | 190 |
| aromatic | propyl | H | β 5-ring + 4'R-methyl | 38513 | 0.2 | — | 2000 | >125 | ND |

NC Not Competitive; ND Not Determined;

What is claimed is:

1. A steroid compound having the formula

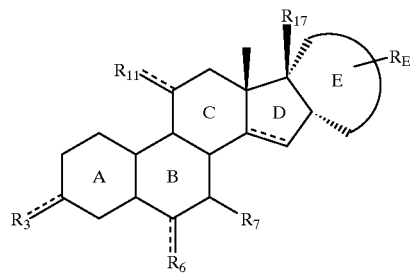

wherein
R$_3$ is =O; —OH; =NOR; —OR or OOCR, in which R is an alkyl group having 1 to 6 carbon atoms;
R$_6$ is H; =CH$_2$ or —(CH$_2$)$_m$H with m is 1 or 2;
R$_7$ is H; C$_{1-4}$-alkyl; C$_{2-5}$-alkenyl or C$_{2-5}$-alkynyl, wherein the alkyl, alkenyl or alkynyl group may be substituted with 1 to 3 halogen atoms independently selected from the group consisting of fluorine and chlorine atoms;
R$_{11}$ is H;
E represents, together with carbon atoms 16 and 17 of ring D, a four to seven-membered ring, said ring being α with respect to the D-ring, substituted with R$_E$ and optionally comprising one or two endocyclic double bonds;
R$_E$ is H; C$_{1-6}$-alkyl; C$_{2-6}$-alkenyl; C$_{2-6}$-alkynyl; C$_{1-6}$-alkylidene; C$_{2-6}$-spiro-anellated cycloalkyl; —OR'; —SR'; —OOCR'; —NHR'; —NR'R'; —NHCOR', wherein R' (and in the case of R$_E$ being —NR'R' each R' independently of the other) is an alkyl with 1 to 6 carbon atoms; —NCO; —(CH$_2$)$_n$—N$_3$ or —(CH$_2$)$_n$—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms;
R$_{17}$ is —OH; —OCH$_2$OR; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic.

2. A steroid compound according to claim 1, wherein the E-ring is a six-membered ring.

3. A steroid compound according to claim 1, wherein R$_7$ is α-propyl, the E-ring is a six-membered ring, R$_3$ and R$_{17}$ are OH, and R$_6$, R$_{11}$, and R$_E$ are H.

4. A steroid compound having the formula

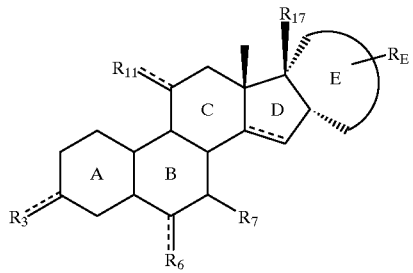

wherein
R$_3$ is =O; —OH; =NOR; —OR or OOCR, in which R is an alkyl group having 1 to 6 carbon atoms;
R$_6$ is H; =CH$_2$ or —(CH$_2$)$_m$H with m is 1 or 2;

R$_7$ is H; C$_{1-4}$-alkyl; C$_{2-5}$-alkenyl or C$_{2-5}$-alkynyl, wherein the alkyl, alkenyl or alkynyl group may be substituted with 1 to 3 halogen atoms independently selected from the group consisting of fluorine and chlorine atoms;

R$_{11}$ is H; C$_{1-4}$-alkyl; C$_{2-4}$-alkenyl; C$_{2-4}$-alkynyl or C$_{1-4}$-alkylidene, wherein the alkyl, alkenyl, alkynyl or alkylidene group may be substituted with 1 to 3 halogen atoms independently selected from the group consisting of fluorine and chlorine atoms;

E represents, together with carbon atoms 16 and 17 of ring D, a four to seven-membered ring, said ring being α with respect to the D-ring, substituted with R$_E$ and optionally comprising one or two endocyclic double bonds;

R$_E$ is H; C$_{1-6}$-alkyl; C$_{2-6}$-alkenyl; C$_{2-6}$-alkynyl; C$_{1-6}$-alkylidene; C$_{2-6}$-spiro-anellated cycloalkyl; —OR'; —SR'; —OOCR'; —NHR'; —NR'R'; —NHCOR', wherein R' (and in the case of R$_E$ being —NR'R' each R' independently of the other) is an alkyl with 1 to 6 carbon atoms; —NCO; —(CH$_2$)$_n$—N$_3$ or —(CH$_2$)$_n$—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms;

R$_{17}$ is —OH; —OCH$_2$OR; —OR or —OOCR wherein R is an alkyl with 1 to 6 carbon atoms; wherein the steroid compound optionally may have one or more double bonds chosen from the group of Δ5(10); Δ4(5); Δ11(12); Δ14(15); or any of the rings A or B may be aromatic.

5. A steroid compound according to claim 4, wherein the E-ring is a six-membered ring.

6. A steroid compound according to claim 4, wherein R$_7$ is α-propyl, the E-ring is a six-membered ring, R$_3$ and R$_{17}$ are OH, and R$_6$, R$_{11}$, and R$_E$ are H.

7. A pharmaceutical composition comprising the steroid compound according to any one of claims 1 to 6, and a pharmaceutically acceptable auxiliary.

8. A method for treating or preventing peri-menopausal or post-menopausal complaints, comprising administering to a person in need thereof an effective amount of a steroid compound having the formula

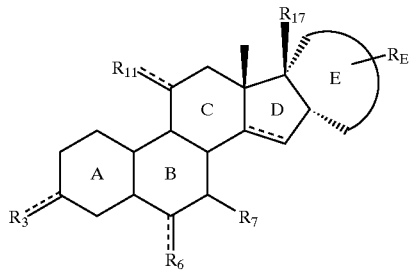

wherein

R$_3$ is =O; —OH; =NOR; —OR or OOCR, in which R is an alkyl group having 1 to 6 carbon atoms;

R$_6$ is H; =CH$_2$ or —(CH$_2$)$_m$H with m is 1 or 2;

R$_7$ is H; C$_{1-4}$-alkyl; C$_{2-5}$-alkenyl or C$_{2-5}$-alkynyl, wherein the alkyl, alkenyl or alkynyl group may be substituted with 1 to 3 halogen atoms independently selected from the group consisting of fluorine and chlorine atoms;

R$_{11}$ is H; C$_{1-4}$-alkyl; C$_{2-4}$-alkenyl; C$_{2-4}$-alkynyl or C$_{1-4}$-alkylidene, wherein the alkyl, alkenyl, alkynyl or alkylidene group may be substituted with 1 to 3 halogen atoms independently selected from the group consisting of fluorine and chlorine atoms;

E represents, together with carbon atoms 16 and 17 of ring D, a four to seven-membered ring, said ring being α with respect to the D-ring, substituted with R$_E$ and optionally comprising one or two endocyclic double bonds;

R$_E$ is H; C$_{1-6}$-alkyl; C$_{2-6}$-alkenyl; C$_{2-6}$-alkynyl; C$_{1-6}$-alkylidene; C$_{2-6}$-spiro-anellated cycloalkyl; —OR'; —SR'; —OOCR'; —NHR'; —NR'R'; —NHCOR', wherein R' (and in the case of R$_E$ being —NR'R' each R' independently of the other) is an alkyl with 1 to 6 carbon atoms; —NCO; —(CH$_2$)$_n$—N$_3$ or —(CH$_2$)$_n$—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms; R$_{17}$ is —OH; —OCH$_2$OR; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic.

9. A method of contraception, comprising administering to a subject in need thereof a contraceptive amount of a steroid compound having the formula

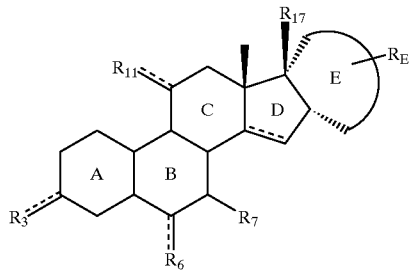

wherein

R$_3$ is =O; —OH; =NOR; —OR or OOCR, in which R is an alkyl group having 1 to 6 carbon atoms;

R$_6$ is H; =CH$_2$ or —(CH$_2$)$_m$H with m is 1 or 2;

R$_7$ is H; C$_{1-4}$-alkyl; C$_{2-5}$-alkenyl or C$_{2-5}$-alkynyl, wherein the alkyl, alkenyl or alkynyl group may be substituted with 1 to 3 halogen atoms independently selected from the group consisting of fluorine and chlorine atoms;

R$_{11}$ is H; C$_{1-4}$-alkyl; C$_{2-4}$-alkenyl; C$_{2-4}$-alkynyl or C$_{1-4}$-alkylidene, wherein the alkyl, alkenyl, alkynyl or alkylidene group may be substituted with 1 to 3 halogen atoms independently selected from the group consisting of fluorine and chlorine atoms;

E represents, together with carbon atoms 16 and 17 of ring D, a four to seven-membered ring, said ring being α with respect to the D-ring, substituted with R$_E$ and optionally comprising one or two endocyclic double bonds;

R$_E$ is H; C$_{1-6}$-alkyl; C$_{2-6}$-alkenyl; C$_{2-6}$-alkynyl; C$_{1-6}$-alkylidene; C$_{2-6}$-spiro-anellated cycloalkyl; —OR';

—SR'; —OOCR'; —NHR'; —NR'R'; —NHCOR', wherein R' (and in the case of $R_E$ being —NR'R' each R' independently of the other) is an alkyl with 1 to 6 carbon atoms; —NCO; —(CH$_2$)$_n$—N$_3$ or —(CH$_2$)$_n$—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms; $R_{17}$ is —OH; —OCH$_2$OR; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic.

10. A method for treating or preventing osteoporosis, comprising administering to a person in need thereof an effective amount of a steroid compound having the formula

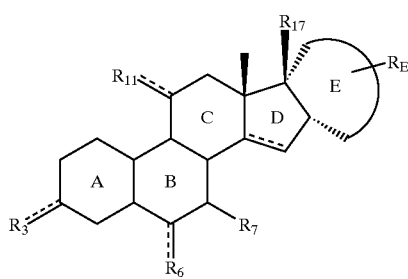

wherein $R_3$ is =O; —OH; =NOR; —OR or OOCR, in which R is an alkyl group having 1 to 6 carbon atoms;

$R_6$ is H; =CH$_2$ or —(CH$_2$)$_m$H with m is 1 or 2;

$R_7$ is H; $C_{1-4}$-alkyl; $C_{2-5}$-alkenyl or $C_{2-5}$-alkynyl, wherein the alkyl, alkenyl or alkynyl group may be substituted with 1 to 3 halogen atoms independently selected from the group consisting of fluorine and chlorine atoms;

$R_{11}$ is H; $C_{1-4}$-alkyl; $C_{2-4}$-alkenyl; $C_{2-4}$-alkynyl or $C_{1-4}$-alkylidene, wherein the alkyl, alkenyl, alkynyl or alkylidene group may be substituted with 1 to 3 halogen atoms independently selected from the group consisting of fluorine and chlorine atoms;

E represents, together with carbon atoms 16 and 17 of ring D, a four to seven-membered ring, said ring being α with respect to the D-ring, substituted with $R_E$ and optionally comprising one or two endocyclic double bonds;

$R_E$ is H; $C_{1-6}$-alkyl; $C_{2-6}$-alkenyl; $C_{2-6}$-alkynyl; $C_{1-6}$-alkylidene; $C_{2-6}$-spiro-anellated cycloalkyl; —OR'; —SR'; —OOCR'; —NHR'; —NR'R'; —NHCOR', wherein R' (and in the case of $R_E$ being —NR'R' each R' independently of the other) is an alkyl with 1 to 6 carbon atoms; —NCO; —(CH$_2$)$_n$—N$_3$ or —(CH$_2$)$_n$—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms; $R_{17}$ is —OH; —OCH$_2$OR; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic.

11. A method for providing an estrogenic and/or progestagenic effect, comprising administering to a subject in need thereof an effective amount of a steroid compound having the formula

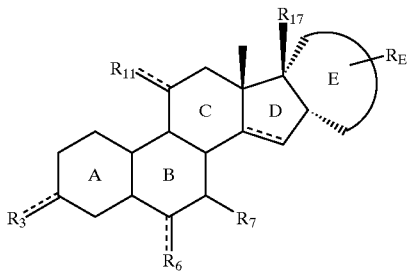

wherein $R_3$ is =O; —OH; =NOR; —OR or OOCR, in which R is an alkyl group having 1 to 6 carbon atoms;

$R_6$ is H; =CH$_2$ or —(CH$_2$)$_m$H with m is 1 or 2;

$R_7$ is H; $C_{1-4}$-alkyl; $C_{2-5}$-alkenyl or $C_{2-5}$-alkynyl, wherein the alkyl, alkenyl or alkynyl group may be substituted with 1 to 3 halogen atoms independently selected from the group consisting of fluorine and chlorine atoms;

$R_{11}$ is H; $C_{1-4}$-alkyl; $C_{2-4}$-alkenyl; $C_{2-4}$-alkynyl or $C_{1-4}$-alkylidene, wherein the alkyl, alkenyl, alkynyl or alkylidene group may be substituted with 1 to 3 halogen atoms independently selected from the group consisting of fluorine and chlorine atoms;

E represents, together with carbon atoms 16 and 17 of ring D, a four to seven-membered ring, said ring being α with respect to the D-ring, substituted with $R_E$ and optionally comprising one or two endocyclic double bonds;

$R_E$ is H; $C_{1-6}$-alkyl; $C_{2-6}$-alkenyl; $C_{2-6}$-alkynyl; $C_{1-6}$-alkylidene; $C_{2-6}$-spiro-anellated cycloalkyl; —OR'; —SR'; —OOCR'; —NHR'; —NR'R'; —NHCOR', wherein R' (and in the case of $R_E$ being —NR'R' each R' independently of the other) is an alkyl with 1 to 6 carbon atoms; —NCO; —(CH$_2$)$_n$—N$_3$ or —(CH$_2$)$_n$—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms; $R_{17}$ is —OH; —OCH$_2$OR; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic.

12. A method for stimulating estrogen and/or progesterone receptors in a subject, comprising administering to the subject in need thereof an effective amount of a steroid having the formula

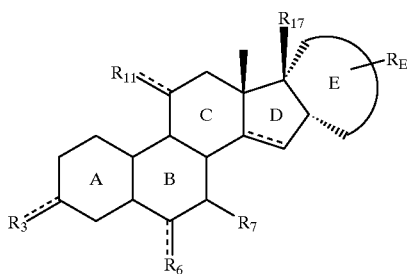

wherein
R₃ is =O; —OH; =NOR; —OR or OOCR, in which R is an alkyl group having 1 to 6 carbon atoms;

$R_6$ is H; =CH₂ or —(CH₂)ₘH with m is 1 or 2;

$R_7$ is H; $C_{1-4}$-alkyl; $C_{2-5}$-alkenyl or $C_{2-5}$-alkynyl, wherein the alkyl, alkenyl or alkynyl group may be substituted with 1 to 3 halogen atoms independently selected from the group consisting of fluorine and chlorine atoms;

$R_{11}$ is H; $C_{1-4}$-alkyl; $C_{2-4}$-alkenyl; $C_{2-4}$-alkynyl or $C_{1-4}$-alkylidene, wherein the alkyl, alkenyl, alkynyl or alkylidene group may be substituted with 1 to 3 halogen atoms independently selected from the group consisting of fluorine and chlorine atoms;

E represents, together with carbon atoms 16 and 17 of ring D, a four to seven-membered ring, said ring being α with respect to the D-ring, substituted with $R_E$ and optionally comprising one or two endocyclic double bonds;

$R_E$ is H; $C_{1-6}$-alkyl; $C_{2-6}$-alkenyl; $C_{2-6}$-alkynyl; $C_{1-6}$-alkylidene; $C_{2-6}$-spiro-anellated cycloalkyl; —OR'; —SR'; —OOCR'; —NHR'; —NR'R'; —NHCOR', wherein R' (and in the case of $R_E$ being —NR'R' each R' independently of the other) is an alkyl with 1 to 6 carbon atoms; —NCO; —(CH₂)ₙ—N₃ or —(CH₂)ₙ—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms;

R₁₇ is —OH; —OCH₂OR; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic, comprising the steps of taking a 17-keto steroid having the formula:

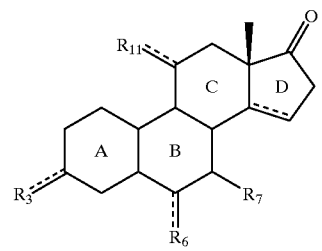

wherein the substituent groups have the meaning above, and attaching, on carbon atom 16, adjacent to the 17-keto moiety, an alkyl chain, substituted or not, suitably functionalized so as to obtain an ω-iodoalkyl moiety, and bringing about the ring-closure of the ω-iodoalkyl moiety by treatment with an organometallic reagent.

14. A process for the preparation of a 16,17 anellated steroid compound having the formula

--- wherein
R₃ is =O; —OH; =NOR; —OR or OOCR, in which R is an alkyl group having 1 to 6 carbon atoms;

$R_6$ is H; =CH₂ or —(CH₂)ₘH with m is 1 or 2;

$R_7$ is H; $C_{1-4}$-alkyl; $C_{2-5}$-alkenyl or $C_{2-5}$-alkynyl, wherein the alkyl, alkenyl or alkynyl group may be substituted with 1 to 3 halogen atoms independently selected from the group consisting of fluorine and chlorine atoms;

$R_{11}$ is H; $C_{1-4}$-alkyl; $C_{2-4}$-alkenyl; $C_{2-4}$-alkynyl or $C_{1-4}$-alkylidene, wherein the alkyl, alkenyl, alkynyl or alkylidene group may be substituted with 1 to 3 halogen atoms independently selected from the group consisting of fluorine and chlorine atoms;

E represents, together with carbon atoms 16 and 17 of ring D, a four to seven-membered ring, said ring being α with respect to the D-ring, substituted with $R_E$ and optionally comprising one or two endocyclic double bonds;

$R_E$ is H; $C_{1-6}$-alkyl; $C_{2-6}$-alkenyl; $C_{2-6}$-alkynyl; $C_{1-6}$-alkylidene; $C_{2-6}$-spiro-anellated cycloalkyl; —OR'; —SR'; —OOCR'; —NHR'; —NR'R'; —NHCOR', wherein R' (and in the case of $R_E$ being —NR'R' each R' independently of the other) is an alkyl with 1 to 6 carbon atoms; —NCO; —(CH₂)ₙ—N₃ or —(CH₂)ₙ—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms; R₁₇ is —OH; —OCH₂OR; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic.

13. A process for the preparation of 16,17 anellated steroid compound having the formula

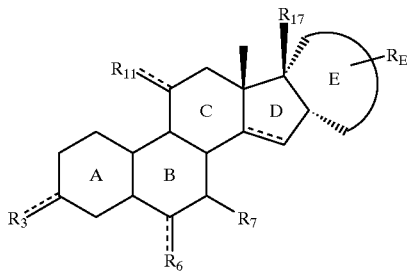

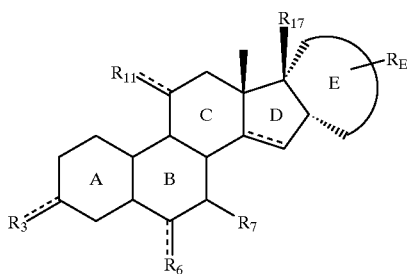

wherein

- $R_3$ is =O; —OH; =NOR; —OR or OOCR, in which R is an alkyl group having 1 to 6 carbon atoms;
- $R_6$ is H; =$CH_2$ or —$(CH_2)_m$H with m is 1 or 2;
- $R_7$ is H; $C_{1-4}$-alkyl; $C_{2-5}$-alkenyl or $C_{2-5}$-alkynyl, wherein the alkyl, alkenyl or alkynyl group may be substituted with 1 to 3 halogen atoms independently selected from the group consisting of fluorine and chlorine atoms;
- $R_{11}$ is H; $C_{1-4}$-alkyl; $C_{2-4}$-alkenyl; $C_{2-4}$-alkynyl or $C_{1-4}$-alkylidene, wherein the alkyl, alkenyl, alkynyl or alkylidene group may be substituted with 1 to 3 halogen atoms independently selected from the group consisting of fluorine and chlorine atoms;
- E represents, together with carbon atoms 16 and 17 of ring D, a four to seven-membered ring, said ring being α with respect to the D-ring, substituted with $R_E$ and optionally comprising one or two endocyclic double bonds;
- $R_E$ is H; $C_{1-6}$-alkyl; $C_{2-6}$-alkenyl; $C_{2-6}$-alkynyl; $C_{1-6}$-alkylidene; $C_{2-6}$-spiro-anellated cycloalkyl; —OR'; —SR'; —OOCR'; —NHR'; —NR'R'; —NHCOR', wherein R' (and in the case of $R_E$ being —NR'R' each R' independently of the other) is an alkyl with 1 to 6 carbon atoms; —NCO; —$(CH_2)_n$—$N_3$ or —$(CH_2)_n$—CN, with n is 0 to 5, wherein the alkyl, alkenyl, alkynyl, alkylidene or cycloalkyl group may be substituted with 1 to 3 substituents independently selected from the group consisting of —OR'; —SR'; —OOCR'; —NHR'; —NR'R'; —NHCOR', with R' being defined as above; fluorine atoms and chlorine atoms;
- $R_{17}$ is —OH; —$OCH_2OR$; —OR or —OOCR wherein R is an alkyl with 1 to 6 carbon atoms; wherein the steroid compound optionally may have one or more double bonds chosen from the group of Δ9(10); Δ5(10); Δ4(5); Δ11(12); Δ14(15); or any of the rings A or B may be aromatic, comprising taking a 17-keto steroid having the formula:

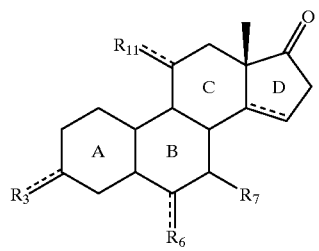

wherein the substituent groups have the meaning above and attaching, on each of the carbon atoms 16 and 17, an alkenyl chain substituted or not, and bringing about the ring-closure via olefin metathesis, using a catalyst derived from a transition metal.

* * * * *